(12) United States Patent
Chiang

(10) Patent No.: US 7,423,753 B1
(45) Date of Patent: Sep. 9, 2008

(54) FIBER OPTICAL SENSOR WITH OPTICAL RESONATOR

(75) Inventor: Huihua Kenny Chiang, Taipei (TW)

(73) Assignee: National Yang-Ming University, Taipei (TW)

(*) Notice: Subject to any disclaimer, the term of this patent is extended or adjusted under 35 U.S.C. 154(b) by 0 days.

(21) Appl. No.: 11/729,782

(22) Filed: Mar. 30, 2007

(51) Int. Cl.
*G01N 21/64* (2006.01)

(52) U.S. Cl. ............ 356/417; 250/458.1; 436/172; 422/82.08

(58) Field of Classification Search .......... 356/417, 356/303, 317, 326; 385/12; 435/288.7, 808; 422/82.07, 82.08; 436/172
See application file for complete search history.

(56) References Cited

U.S. PATENT DOCUMENTS 4,447,546 A * 5/1984 Hirschfeld ........... 436/527
5,528,040 A * 6/1996 Lehmann ............. 250/343
5,841,801 A * 11/1998 Suzuki ................ 372/23
2004/0233458 A1 * 11/2004 Frick ................. 356/480

* cited by examiner

*Primary Examiner*—F. L. Evans
*Assistant Examiner*—Abdullahi Nur
(74) *Attorney, Agent, or Firm*—Muncy, Geissler, Olds & Lowe, PLLC

(57) ABSTRACT

A fiber optical sensor includes a light source, a detector and an optical resonator having a multimode optical fiber and two reflective layers respectively provided adjacent to or on ends of the optical fiber. Excitation light from the light source is coupled into the optical resonator through a transparent hole formed in one of the reflective layers. An evanescent wave extends outside the optical fiber in the active region of the optical fiber. The fluorescent light generated by a fluorescent material excited by the evanescent wave in response to the presence or concentration of the analyte in a sample to be assayed is detected by the detector. The light beam is reflected back and forth between the first and second reflective layers many times within the optical resonator whereby the strength of the fluorescent light is significantly increased thereby resulting in a significantly signal amplification.

23 Claims, 2 Drawing Sheets

FIBER OPTICAL SENSOR WITH OPTICAL RESONATOR

BACKGROUND OF THE INVENTION

1. Field of the Invention

This invention relates to fiber optical sensors, and more specifically to evanescent-wave fiber optical sensors.

2. Description of the Related Art

Fiber optical sensors are analytical devices in which an optical fiber serves as a transduction device. With the advent of optical transducers, better electronics, and improved immobilization methods, fiber optical sensors are being increasingly applied to industrial process and environmental monitoring, food processing, and clinical applications. These fiber optical sensors have specific advantages such as geometrical versatility, remote-sensing capability, small dimensions, and light weight.

Evanescent-wave fiber optical sensor are a class of fluorescence-based fiber optical sensors that selectively measure the fluorescence of fluorescent materials immobilized onto a surface of the optical fiber by use of the evanescent wave. The evanescent wave is associated with an electromagnetic field propagating in the optical fiber and typically penetrates from a few tens nanometers to several hundred nanometers into the medium surrounding the optical fiber, when the cladding layer of the optical fiber is removed. This evanescent wave can locally excite the fluorescent materials when they are bound by molecules on or very close to the optical fiber surface. This fluorescence technique can lead to an efficient and selective immunoassay or hybridization assay.

However, evanescent-wave fiber optical sensors have demonstrated inadequate sensitivity. Specifically, this is attributed at least in part to the effects of a weak evanescent wave that only allows a small percent of its light to excite the fluorescent materials on or near the fiber surface.

SUMMARY OF THE INVENTION

It is therefore an object of the present invention to provide evanescent-wave fiber optical sensors having a high sensitivity.

To achieve the above listed and other objects, an evanescent-wave fiber optical sensor having features of the present invention generally is provided with an optical resonator capable of increasing the power of the excitation light penetrating into the sample to be assayed thereby increasing the amount of fluorescent light and sensor sensitivity.

Specifically, the optical resonator of the present invention includes a multimode optical fiber, a first reflective layer adjacent to or on one end of the optical fiber and a second reflective layer adjacent to or on the other end of the optical fiber. The first reflective layer having a small transparent hole defined therein. The surface of the optical fiber has an active region with a property of binding with the analyte when brought in contact with the analyte. Excitation light emitted from a light source is coupled into the optical resonator through the small transparent hole and the evanescent wave is generated at the active region of the optical fiber. The fluorescent light generated from a fluorescent material excited by the evanescent wave in response to the presence or concentration of the analyte in the sample is detected by a detector.

Note that, after the light beam enters the optical resonator through the small transparent hole, the light beam is reflected back and forth between the first and second reflective layers many times. Each time the light beam propagates in the optical fiber, a portion of its power is transformed from the evanescent wave into the fluorescent light. The more times the light beam propagates in the optical fiber, the larger percentage of its power is transformed into the fluorescent light. Therefore, the total strength of the fluorescent light is significantly increased by providing the optical resonator of the present invention thereby increasing sensor sensitivity.

The reflective layers may be realized by a multilayer dielectric high reflective coating on two ends of the optical fiber, or attaching two mirrors with multilayer dielectric high reflective coating thereon to two ends of the optical fiber. Alternatively, the reflective layers may be realized by forming metal coatings on two ends of the optical fiber.

According to one aspect of the present invention, the active region of the optical fiber may comprise attached biomolecular species that recognizes the analyte. The fluorescent material may be a fluorescent molecule that recognizes the analyte bound to the active region of the optical fiber.

According to another aspect of the present invention, the fluorescent material may be attached on the active region and the fluorescent properties of the fluorescent material change in response to the presence or concentration of the analyte, such as by fluorescence quenching upon binding of the analyte to the fluorescent material.

According to still another aspect of the present invention, the active region of the optical fiber comprises attached biomolecular species that recognizes the analyte, and the fluorescent material is an analog of the analyte. Therefore, the presence or concentration of the analyte in the sample can be detected by measurement of the competitive binding of the analyte versus the fluorescent analog to the biomolecular species attached to the active region of the optical fiber.

BRIEF DESCRIPTION OF THE DRAWINGS

These and other features, aspects, and advantages of the present invention will be more fully understood by reading the following detailed description of the preferred embodiment, with reference made to the accompanying drawings as follows.

DETAILED DESCRIPTION OF THE PREFERRED EMBODIMENT

The present invention is directed to an evanescent-wave fiber optical sensor provided with an optical resonator capable of increasing the total strength of the evanescent wave penetrating into the sample to be assayed thereby increasing the amount of fluorescent light and sensor sensitivity. Typically, the fiber optical sensor is provided with a light source and a detector for detecting the fluorescent light generated by a fluorescent material in response to the presence or concentration of the analyte in the sample.

Figure 1:
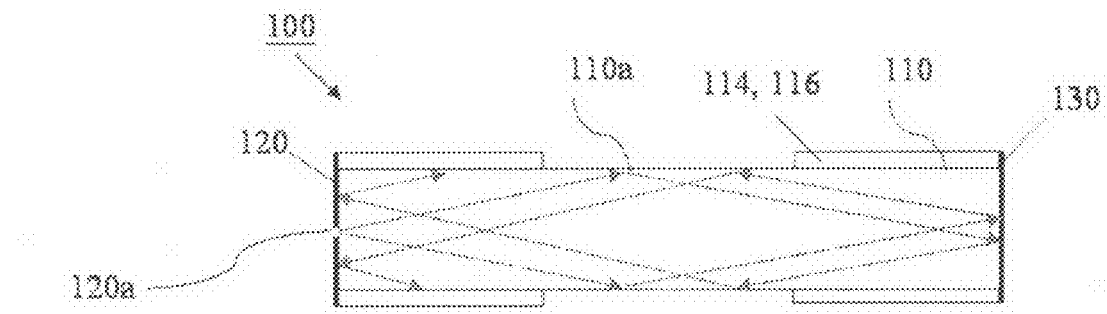
FIG. 1 is a cross sectional view of a optical resonator according to one embodiment of the present invention.

FIG. 1 shows an optical resonator 100 according to one embodiment of the present invention. As shown, the optical resonator 100 mainly includes a multimode optical fiber 110, a first reflective layer 120 adjacent to or on one end of the optical fiber 110 and a second reflective layer 130 adjacent to or on the other end of the optical fiber 110.

The reflective layer may be any material that reflects light at the excitation wavelength. Typically, the reflective layer includes a reflective metal, such as aluminum, silver, chromium, platinum or mixtures thereof. Preferably, the reflective layer may be a multilayer dielectric high reflective coating that can produce very high reflection at designed wavelength. The reflective layer may be provided adjacent to or on the optical fiber 110 in any manner. As shown in FIG. 1, the reflective layers 120 and 130 are realized by forming multilayer dielectric high reflective coatings on two ends of the optical fiber 110. Alternatively, the reflective layers may be realized by placing two mirrors with reflective metal thereon to two ends of the optical fiber.

The first reflective layer 120 having a transparent hole 120a through which excitation light emitted from a light source (shown in FIG. 2) is coupled into the optical resonator 100. The diameter of the hole 120a needs to be much smaller than the diameter of the optical fiber 110, in order to reduce the amount of the excitation light leaking out of the hole after it is reflected backward from the other reflective layer 130. The preferred diameter of the hole is between 1 micrometer and up to $1/15$ of the diameter of the optical fiber. If the diameter is less than 1 micrometer, it will cause difficulties in the fabricating of the hole as well as in the coupling of the excitation light into the hole. The upper limit of the diameter of the hole is determined by the diameter of the optical fiber 110. The diameters of multimode optical fibers are usually between 50 to 1000 micrometers. For a smaller diameter fiber (e.g., 50 micrometers in diameter), a smaller hole is preferred (e.g., a hole having the diameter of $1/15$ of the fiber diameter); this arrangement reflects $224/225$ ($=1-1/15^2$) of the backward propagating excitation light back to the optical fiber. For a larger diameter fiber (e.g., 1000 micrometers in diameter), a larger hole can be allowed (e.g., a hole having the diameter of $1/100$ of the fiber diameter; nearly $9999/10000$ ($=1-1/100^2$) of the backward propagating excitation light will be reflected back to the optical fiber. The transparent hole 120a may be formed by laser drilling or etching away a central part of the reflective layer 120. A reflective coating may be applied to the surface of the waveguide in any manner. Other methods for patterning metal or other reflective layer may be used to form the reflective layer 120 with the transparent hole 120a defined therein, e.g., masked vacuum evaporation of the reflective coating, photolithography, and electroless deposition. The same or similar processes may be used to provide the reflective layer as a multilayer structure.

The surface of the optical fiber 110 has an active region 110a with a property of binding with an analyte in a sample to be assayed when brought in contact with the analyte. In one embodiment, a multimode silica fiber with a core diameter of several hundred micrometers is used in fabrication of the optical resonator 100. The optical fiber is pre-treated as described below. Initially, a suitable length (e.g., around 5-cm length) of the buffer layer 114 of the bare optical fiber is removed by means of a high temperature flame. After the treated fiber is washed by acetone and ethanol, the exposed fiber cladding layer 116 is removed by chemical etching, e.g., by immersion of the fiber in a 20:1 $NH_4F(40\%):HF(51\%)$ solution.

Thereafter, the unclad region of the optical fiber 110 is further treated to become the active region 110a by attachment with or otherwise coating with species that recognizes the analyte. The recognition species may be a protein (e.g., antibody against the analyte and cell receptor proteins that recognizes the analyte), a nucleic acid (e.g., DNA and RNA), cell, or cell fragment. The attachment of molecular recognition species to the unclad surface of the optical fiber 110 may be accomplished via using surface activation agents such as aminopropyltriethoxysilane (ATPS). Detailed procedures described in *Appl. Biochem. And Biotech.* 22, 311-330, 1989 and *Appl. Biochem. And Biotech.* 41, 157-188, 1993 are incorporated herein by reference.

Any type of bioaffinity/chemical assay, e.g., a sandwich assay, a competitive assay or a fluorescence quenching assay, is suitable for use in the present invention. In a sandwich assay, the analyte in a sample binds to a primary biomolecular recognition specie on the active region 110a of the optical fiber 110, and then a labeled secondary molecular specie binds to the immobilized analyte or the immobilized analyte/primary molecular species complex. In a competitive assay, unlabeled analyte compete for open binding sites on the active region 110a of the optical fiber 110 that has been previously saturated with labeled analyte. In a fluorescence quenching assay, fluorescence quenching occurs upon binding of the analyte to labeled recognition species on the active region 110a of the optical fiber 110.

Regardless of how analyte assay is achieved, the label used in the present invention is a fluorescent label on or nearby the active region 110a of the optical fiber 110 thereby capable of being excited by the evanescent wave generated when the excitation light is coupled into the optical resonator 100.

Referring to FIG. 1 again, after the excitation light (indicated by arrows in FIG. 1) enters the hole 120a, it will expand as it propagates along the optical fiber 110. When the light beam reaches the other end of the optical fiber 110, the light beam will be reflected backward by the reflective layer 130. Since the light-entering-end of the optical fiber 110 is also provided with the reflective layer 120, most of the back-reflected light beam will also be reflected backward again. Therefore, once the excitation light enters the hole 120a, it will be reflected back and forth between the first and second reflective layers 120 and 130 many times inside the optical resonator 100 until its energy is fully transformed into fluorescent light, scattering light, or being absorbed. Therefore, this novel optical resonator 100 will allow fully use of the excitation light to excite the fluorescent label on or nearby the active region 110a of the optical fiber 110. Specifically, each time the light beam propagates in the optical fiber, a portion of its power extends outside the optical fiber in the form of the evanescent wave. The more times the light beam propagates in the optical fiber, the larger percentage of its power is transformed into the fluorescent light. Therefore, the strength of the fluorescent light is significantly increased by providing the optical resonator of the present invention thereby increasing the sensor sensitivity.

Figure 2:
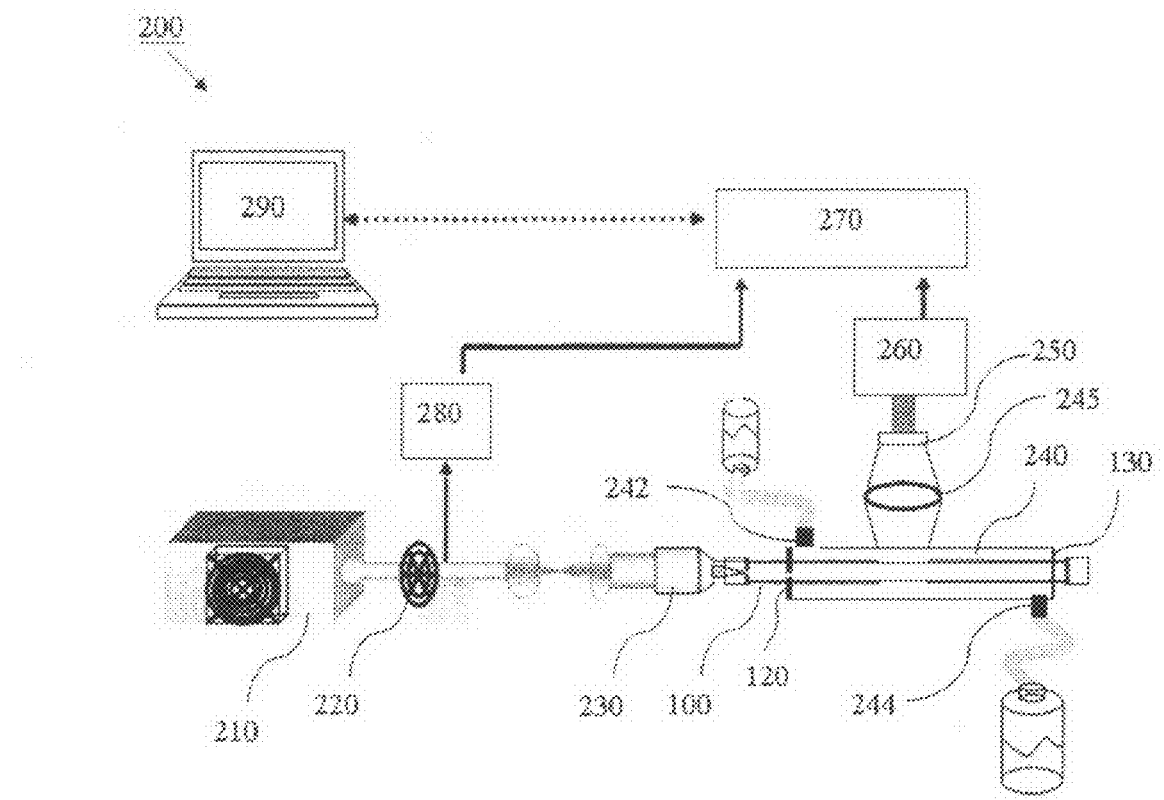
FIG. 2 is a schematic layout of fiber optical sensor utilizing the optical resonator of FIG. 1 according to one embodiment of the present invention.

FIG. 2 shows a fiber optical sensor 200 utilizing the optical resonator 100 of FIG. 1 according to one embodiment of the present invention. As shown, the sensor 200 includes a light source emitting the excitation light to be coupled into the optical resonator 100. An exemplary light source for use with the present invention is a 488 nm excitation laser 210. The laser light beam from the laser 210 is chopped using an optical chopper 220 at a rate of 1 kHz and focused by a microscope Objective Lens 230 onto the proximal end of the optical fiber 110 of the optical resonator 100. The optical resonator 100 is disposed in a flow cell 240 having separate ports 242 and 244 for sample entry and exit. Preferably, the flow cell 240 is a glass flow cell whereby the inside surface thereof has an intrinsic property of not binding to the analyte.

The fluorescent light generated by a fluorescent material excited by the evanescent wave in response to the presence or concentration of the analyte in the sample is collected by a collection lens 245, filtered by a high-pass filter 250 and amplified by a photo multiplier tube 260. The signal from the photo-multiplier tube 260 is processed by a lock-in amplifier 270 (which also receives a reference signal from the chopper controller 280) and the signal from the lock-in amplifier is output to the signal processing apparatus 290.

The total excited fluorescent signal intensity of the present invention can be represented by the following formula I:

$$\begin{aligned}
E_r &= I_0\alpha(1-r) + I_0\alpha(1-r)^2\eta_1 + I_0\alpha\beta(1-r)^3\eta_1\eta_2 + I_0\alpha\beta(1-r)^4\eta_1^2\eta_2 + \\
&\quad I_0\alpha\beta^2(1-r)^5\eta_1^2\eta_2^2 + I_0\alpha\beta^2(1-r)^6\eta_1^3\eta_2^2 + \ldots \\
&= I_0\alpha(1-r) \times \left\{ \begin{array}{l} [1 + \beta(1-r)^2\eta_1\eta_2 + \beta^2(1-r)^4\eta_1^2\eta_2^2 + \ldots] + \\ (1-r)\eta_1[1 + \beta(1-r)^2\eta_1\eta_2 + \beta^2(1-r)^4\eta_1^2\eta_2^2 + \ldots] \end{array} \right\} \\
&= I_0\alpha(1-r) \times \left[ \frac{1}{1-\beta(1-r)^2\eta_1\eta_2} + \frac{(1-r)\eta_1}{1-\beta(1-r)^2\eta_1\eta_2} \right] \\
&= I_0\alpha(1-r) \times \frac{1 + (1-r)\eta_1}{1-\beta(1-r)^2\eta_1\eta_2}
\end{aligned}$$

where $I_0$ represents the initial light intensity coupled into the optical fiber 110, $\alpha$ represents the fluorescence excitation efficiency, $\beta$ is the effective reflection coefficient due to the existence of the hole 120a on the surface of the proximal end of the optical fiber 110, $\gamma$ represents the optical attenuation of the optical fiber 110, $\eta 1$ is the reflectivity of the reflective layer 130, and $\eta 2$ is the reflectivity of the reflective layer 120. According to the formula I, the amplification ratio of the fluorescent signal intensity of the present invention to conventional devices can be represented by the following formula II:

$$\frac{1 + (1-r)\eta_1}{1-\beta(1-r)^2\eta_1\eta_2}$$

In one embodiment, the amplification ratio of the fluorescent signal intensity is around 49, if $\gamma=0.01$, $\eta 1=0.99$, $\eta 2=0.99$, and $\beta \square 0.998$ (i.e., 20 micros diameter hole formed on a 600 micros diameter fiber).

Figure 3:
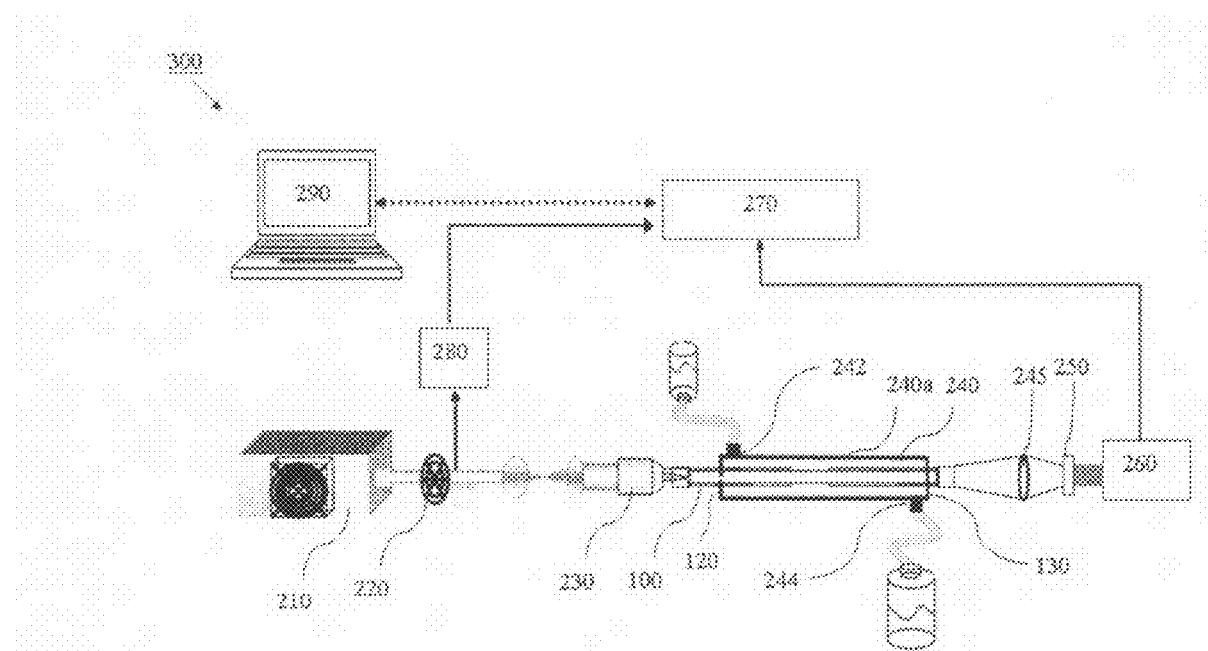
FIG. 3 is a schematic layout of fiber optical sensor utilizing the optical resonator of FIG. 1 according to another embodiment of the present invention.

FIG. 3 shows a fiber optical sensor 300 utilizing the optical resonator 100 of FIG. 1 according to another embodiment of the present invention. The fiber optical sensor 300 is substantially identical to the fiber optical sensor 200 of FIG. 2 except that the reflective layer 130 of the optical resonator 100 is a dichromatic mirror that only reflects the excitation light coupled into the optical resonator 100, while allow the fluorescent light to go straight out to the high-pass filter 250 and then the photo multiplier tube 260. This design is to allow the detection of the fluorescent signal at the light-outputting-end of the optical resonator 100. Furthermore, it is preferable to provide a cylinder mirror 240a inside or outside the flow cell 240 (or a reflective layer on the wall of the flow cell 240) to reflect the fluorescent light back into the optical resonator 100.

Figure 4:
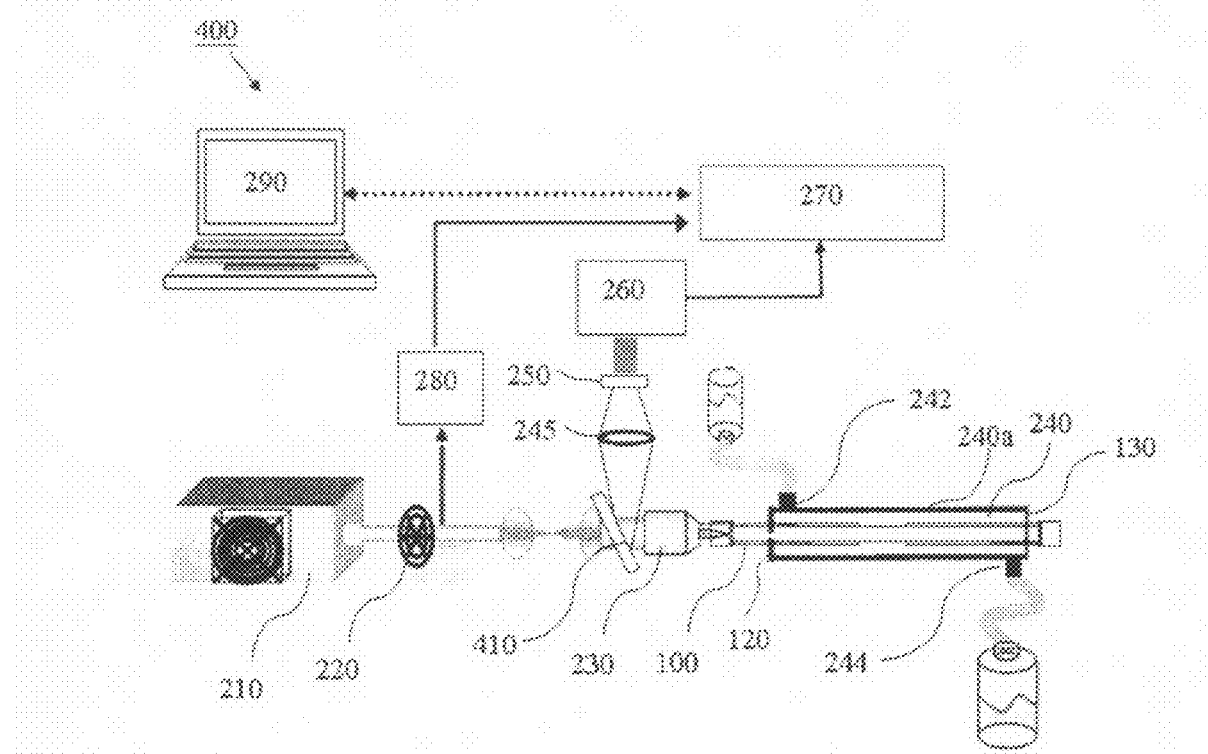
FIG. 4 is a schematic layout of fiber optical sensor utilizing the optical resonator of FIG. 1 according to another embodiment of the present invention.

FIG. 4 shows a fiber optical sensor 400 utilizing the optical resonator 100 of FIG. 1 according to still another embodiment of the present invention. The fiber optical sensor 400 is substantially identical to the fiber optical sensor 200 of FIG. 2 except that (a) a dichromatic mirror 410 is provided between the excitation laser 210 and the optical resonator 100, and (b) the reflective layer 120 of the optical resonator 100 is a dichromatic mirror that only reflects the excitation light coupled into the optical resonator 100, while allow the fluorescent light to go back to the dichromatic mirror 410 that reflects the fluorescent light to the high-pass filter 250 and then the photo multiplier tube 260. This design is to allow the detection of the fluorescent signal at the light-entering-end of the optical resonator 100. The embodiment may be the most convenient design when the sensor is used inside human body or when inserted into some closed chamber, or underground measurements, since there is no need to withdrawal the sample outside to conduct measurement. In this embodiment, it is also preferable to provide a cylinder mirror 240a inside or outside the flow cell 240 (or a reflective layer on the wall of the flow cell 240).

The fiber optical sensor of the present invention exhibits a inherent physical signal amplification due to fully use of the excitation light to excite the fluorescent label by using the optical resonator. The fiber optical sensor of the present invention has the potential to increase the fluorescence yield of labeled biomolecules to about several tens to 100-fold when compared with conventional sensors without the aforementioned optical resonator. The fiber optical sensor of the present invention combines superior sensitivity (due to signal amplification by the optical resonator) with exceptional selectivity (due to the selective chemical binding to the analyte in the sample and the evanescent wave local excitation property).

Although the invention has been explained in relation to its preferred embodiments, it is to be understood that many other possible modifications and variations can be made without departing from the spirit and scope of the invention as hereinafter claimed.

What is claimed is:

1. A fiber optical sensor for detecting an analyte in a sample, the fiber optical sensor comprising:
   an optical resonator having a multimode optical fiber, a first reflective layer adjacent to or on one end of the optical fiber and a second reflective layer adjacent to or on the other end of the optical fiber, the first reflective layer having a transparent hole defined therein;
   the surface of the optical fiber having an active region with a property of binding with the analyte when brought in contact with the analyte;
   a light source emitting excitation light to be coupled into the optical resonator through the transparent hole and the evanescent wave is generated at the active region of the optical fiber;
   a detector for detecting the fluorescent light generated by a fluorescent material excited by the evanescent wave in response to the presence or concentration of the analyte in the sample;
   wherein, after the light beam enters the optical resonator through the transparent hole, the light beam is reflected back and forth between the first and second reflective layers many times whereby the excitation light is effectively used to excite the fluorescent material, and the fluorescent signal is significantly amplified.

2. The fiber optical sensor as claimed in claim 1, wherein each reflective layer includes a reflective metal.

3. The fiber optical sensor as claimed in claim 1, wherein each reflective layer includes a multilayer dielectric high reflective coating.

4. The fiber optical sensor as claimed in claim 1, wherein the first reflective layer reflects both the excitation light coupled into the optical resonator and the fluorescent light, and the second reflective layer is a dichromatic mirror that reflects the excitation light but allows the fluorescent light to pass through.

5. The fiber optical sensor as claimed in claim 1, wherein the first reflective layer is a first dichromatic mirror that reflects the excitation light but allows the fluorescent light to pass through, and the second reflective layer reflects both the excitation light coupled into the optical resonator and the fluorescent light, and the fiber optical sensor further comprising a second dichromatic mirror provided between the light source and the optical resonator wherein the second dichromatic mirror reflects the fluorescent light coming from the first dichromatic mirror.

6. The fiber optical sensor as claimed in claim 1, wherein the active region of the optical fiber comprises attached biomolecular species that recognizes the analyte.

7. The fiber optical sensor as claimed in claim 1, wherein the fluorescent material is a fluorescent molecule that recognizes the analyte bound to the active region of the optical fiber.

8. The fiber optical sensor as claimed in claim 1, wherein the fluorescent material is attached on the active region and the fluorescent properties of the fluorescent material change in response to the presence or concentration of the analyte.

9. The fiber optical sensor as claimed in claim 8, wherein the fluorescent change is accomplished by fluorescence quenching upon binding of the analyte to the fluorescent material.

10. The fiber optical sensor as claimed in claim 1, wherein the active region of the optical fiber comprises attached biomolecular species that recognizes the analyte, and the fluorescent material is an analog of the analyte.

11. The fiber optical sensor as claimed in claim 1, further comprising a flow cell having separate ports for sample entry and exit wherein the optical resonator is disposed in the flow cell.

12. The fiber optical sensor as claimed in claim 1, wherein the transparent hole of the first reflective layer has a diameter larger than 1 micrometer but smaller than $1/15$ of the diameter of the optical fiber.

13. An optical resonator for a fiber optical sensor to detect an analyte in a sample, the fiber optical sensor having a light source and a detector for detecting the fluorescent light generated by a fluorescent material in response to the presence or concentration of the analyte in the sample, the optical resonator comprising:
   a multimode optical fiber;
   a first reflective layer adjacent to or on one end of the optical fiber, the first reflective layer having a transparent hole defined therein; and
   a second reflective layer adjacent to or on the other end of the optical fiber;
   the surface of the optical fiber having an active region with a property of binding with the analyte when brought in contact with the analyte,
   wherein the light source emits excitation light coupling into the optical resonator through the transparent hole such that an evanescent wave is generated at the active region of the optical fiber to excite the fluorescent material, and
   the light beam is reflected back and forth between the first and second reflective layers many times whereby the strength of the fluorescent light is significantly increased thereby resulting in a significantly signal amplification.

14. The optical resonator as claimed in claim 13, wherein each reflective layer includes a reflective metal.

15. The optical resonator as claimed in claim 13, wherein each reflective layer includes a multilayer dielectric high reflective coating.

16. The optical resonator as claimed in claim 13, wherein the first reflective layer reflects both the excitation light coupled into the optical resonator and the fluorescent light, and the second reflective layer is a dichromatic mirror that reflects the excitation light but allows the fluorescent light to pass through.

17. The optical resonator as claimed in claim 13, wherein the first reflective layer is a dichromatic mirror that reflects the excitation light but allows the fluorescent light to pass through, and the second reflective layer reflects both the excitation light coupled into the optical resonator and the fluorescent light.

18. The optical resonator as claimed in claim 13, wherein the fluorescent material is attached on the active region and the fluorescent properties of the fluorescent material change in response to the presence or concentration of the analyte.

19. The optical resonator as claimed in claim 18, wherein the fluorescent change is accomplished by fluorescence quenching upon binding of the analyte to the fluorescent material.

20. The optical resonator as claimed in claim 19, wherein the active region of the optical fiber comprises attached biomolecular species that recognizes the analyte, and the fluorescent material is an analog of the analyte.

21. The optical resonator as claimed in claim 13, wherein the transparent hole of the first reflective layer has a diameter larger than 1 micrometer but smaller than $1/15$ of the diameter of the optical fiber.

22. The optical resonator as claimed in claim 13, wherein the excitation light is coupled into the transparent hold on-axis with the center axis of the multimode optical fiber.

23. The fiber optical sensor as claimed in claim 1, wherein the excitation light is coupled into the transparent hole on-axis with the center axis of the multimode optical fiber.

* * * * *